US00PP34083P2

(12) United States Plant Patent
Kraan

(10) Patent No.: US PP34,083 P2
(45) Date of Patent: Mar. 29, 2022

(54) ***SALVIA* PLANT NAMED 'BOCOFFLA'**

(50) Latin Name: ***Salvia* hybrid**
Varietal Denomination: Bocoffla

(71) Applicant: Kees Jan Kraan, Alphen aan den Rijn (NL)

(72) Inventor: Kees Jan Kraan, Alphen aan den Rijn (NL)

(73) Assignee: BOOT & CO BOOMKWEKERIJEN BV, Boskoop (NL)

( * ) Notice: Subject to any disclaimer, the term of this patent is extended or adjusted under 35 U.S.C. 154(b) by 0 days.

(21) Appl. No.: 17/192,098

(22) Filed: Mar. 4, 2021

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
See application file for complete search history.

(56) References Cited

PUBLICATIONS

PLUTO Plant Variety Database Jun. 24, 2021. p. 1.*

* cited by examiner

*Primary Examiner* — Annette H Para
(74) *Attorney, Agent, or Firm* — Penny J. Aguirre

(57) ABSTRACT

A new cultivar of hybrid *Salvia* plant named 'Bocoffla' that is characterized by its densely branched, compact plant habit, its laciniate shaped leaves, its foliage, peduncles and flowers that are densely pubescent, its flowers that are light pink in color, and its individual flowers that are held in an average angle of 45° to 90° to vertical.

2 Drawing Sheets

Botanical classification: *Salvia* hybrid.
Variety denomination: 'Bocoffla'.

CROSS REFERENCE TO A RELATED APPLICATION

This application is related to a European plant breeders' rights application filed on Nov. 28, 2019, application No. 2019/3174. There have been no offers for sale anywhere in the world prior to the effective filing date of this Application and no accessibility to one of ordinary skill in the art could have been derived from the printed plant breeder's rights documents. This application is co-pending with a U.S. Plant Patent Application filed for a plant derived from the same breeding program that is entitled *Salvia* Plant Named 'Bocofpea' (U.S. Plant patent application Ser. No. 17/192,165).

BACKGROUND OF THE INVENTION

The present invention relates to a new and distinct cultivar of *Salvia* of hybrid origin and will be referred to hereafter by its cultivar name, 'Bocoffla'. 'Bocoffla' is an herbaceous perennial grown for landscape use.

The new *Salvia* arose from a breeding program conducted by the Inventor at a nursery in Boskoop, The Netherlands. The objective of the breeding program was to develop a new *Salvia* cultivar with unique leaf shapes, flower colors and plant shape.

The new *Salvia* originated by allowing open pollination to occur in July of 2015 between an unnamed proprietary seedling of *Salvia jurisicii* as the female parent and various other species and cultivars of *Salvia* planted in the area. The male parent is therefore unknown. 'Bocoffla' was selected as a unique single plant resulting from the resulting seedlings in summer of 2018.

Asexual propagation of the new cultivar was first accomplished by the inventor by stem cuttings for further trials in summer of 2017 in Boskoop, The Netherlands. Asexual propagation by stem cutting has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bocoffla' as a unique cultivar of *Salvia*.

1. 'Bocoffla' exhibits a densely branched, compact plant habit.
2. 'Bocoffla' exhibits laciniate shaped leaves.
3. 'Bocoffla' exhibits foliage, peduncles and flowers that are densely pubescent.
4. 'Bocoffla' exhibits flowers that are light pink in color.
5. 'Bocoffla' exhibits individual flowers that are held in an average angle of 45° to 90° to vertical.

The female parent differs from 'Bocoffla' in having a spreading plant habit, leaves that are pinnatifid to deeply laciniate in shape, foliage, peduncles and flowers that have pubescent hairs that are longer in length, individual flowers that are held in an upside-down angle, and flowers that are dark blue in color. 'Bocoffla' can also be most compared to *Salvia kuznetsovii* 'Pink Form' (not patented), *Salvia nemorosa* 'Sensation Rose' (U.S. Plant Pat. No. 18,230), and *Salvia* 'Bocofpea'. 'Pink Form' is similar to 'Bocoffla' in having flowers that are light pink in color. 'Pink Form' differs from 'Bocoffla' in having a taller plant height, a more open and relatively loose plant shape, entire margins, flowers that are larger in size, and flowers that are held vertical. 'Sensation Rose' is similar to 'Bocoffla' in having flowers that are pink in color. 'Sensation Rose' differs from 'Bocoffla' in having a more spreading plant habit, entire margins, and flowers that are darker pink in color, and held vertical. 'Bocofpea' differs from 'Bocoffla' in having flowers that are light violet to violet-blue in color.

BRIEF DESCRIPTION OF THE DRAWINGS

The accompanying color photographs illustrate the overall appearance and distinct characteristics of a 6-month-old plant of the new *Salvia* as grown in a 15-cm container from 3 plugs per container in Boskoop, The Netherlands.

The photograph in FIG. 1 provides a side view of the plant of 'Bocoffla' in bloom.

Figure 1:
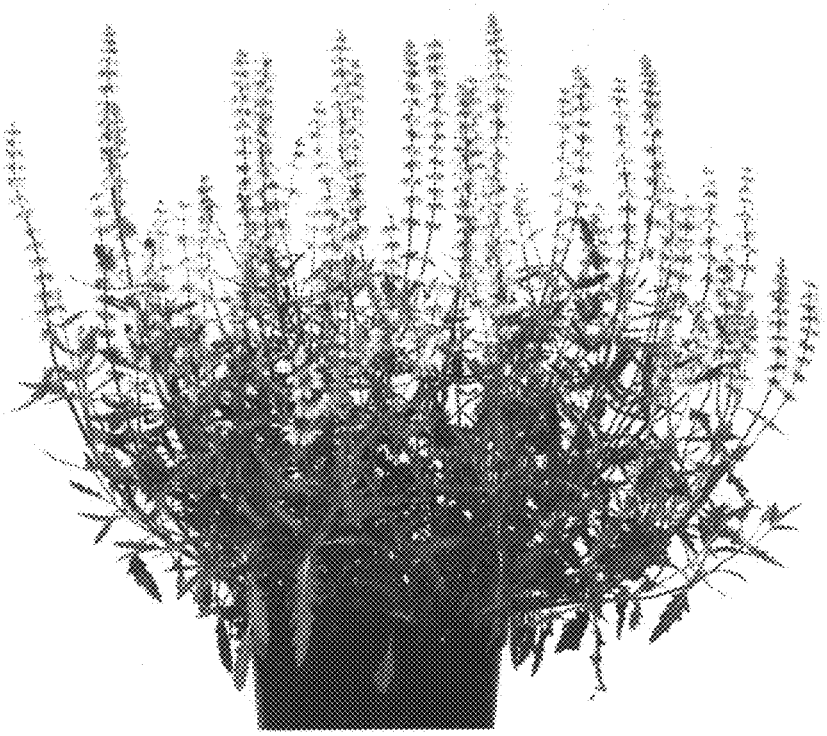
Figure 2:
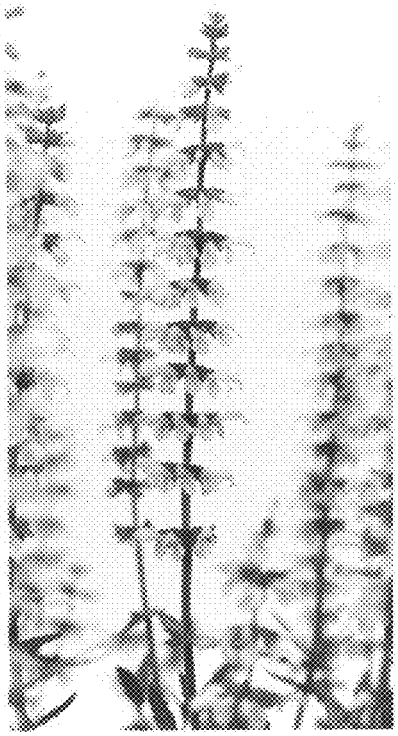

The photograph in FIG. 2 provides a close-up view of an inflorescence of 'Bocoffla'.

Figure 3:
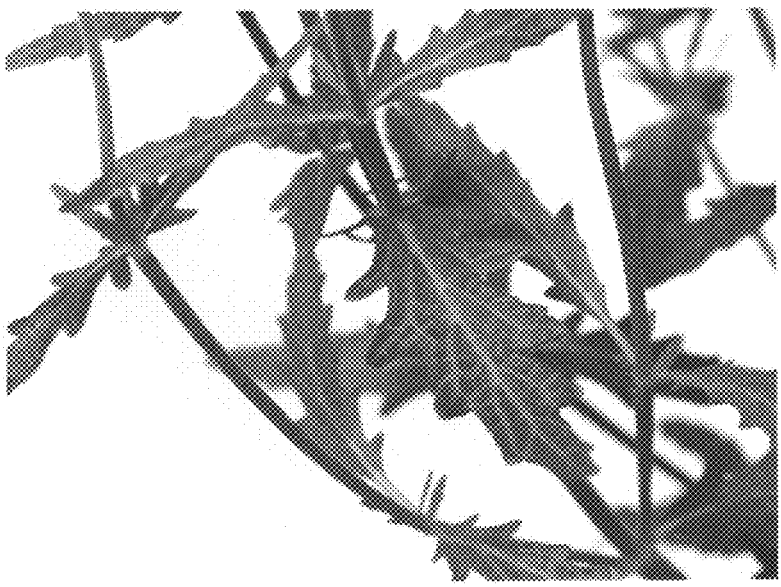

The photograph in FIG. 3 provides a close-up view of the foliage of 'Bocoffla'.

The colors in the photographs may differ slightly from the color values cited in the detailed botanical description, which accurately describe the colors of the new *Salvia*.

DETAILED BOTANICAL DESCRIPTION

The following is a detailed description of the new cultivar 6 months in age as grown outdoors in 15-cm containers from 3 plugs per container in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 4 months from late May to late September in The Netherlands.

*Plant type*.—Herbaceous perennial.

*Plant habit*.—Broadly spreading, upright, densely branched, and compact.

*Plant size*.—Average of 23.7 cm in height (soil level to top of foliar plane), average of 36.5 cm in height (soil level to top of floral plane), 46 cm in spread as grown in a 15 cm container and up to 50 cm in height and spread in the landscape.

*Hardiness*.—At least in U.S.D.A. Zones 4 to 10.

*Diseases and pests*.—No susceptibility or resistance to diseases or pests has been observed.

*Root description*.—Fibrous.

*Propagation*.—Vegetative stem cuttings.

*Growth rate*.—Moderately vigorous.

*Root development*.—20 days for root initiation, 60 days to produce a young plant from rooted cutting.

Stem description:

*Shape*.—4-angled.

*Stem color*.—New growth; 143B, mature stems; 138A.

*Stem size*.—Average of 17.8 cm in length (excluding inflorescence), 2 mm in diameter.

*Stem surface*.—Slightly glossy, moderately covered with short hairs, average of 1.5 mm in length, N155A in color.

*Stem fragrance*.—When rubbed, the stems are pleasantly fragrant.

*Internode length*.—Average of 4.5 cm.

*Branching*.—Average of 9 primary branches, 45 secondary branches.

Foliage description:

*Leaf shape*.—Narrowly ovate to narrowly oblong and laciniate.

*Leaf division*.—Simple.

*Leaf base*.—Acuminate.

*Leaf apex*.—Acute.

*Leaf fragrance*.—None.

*Leaf venation*.—Pinnate, 143C in color on upper surface, 145A in color on lower surface.

*Leaf margins*.—Crenate, lobed; shallow to medium, divergent.

*Leaf arrangement*.—Opposite.

*Leaf attachment*.—Petiolate.

*Leaf surface*.—Both surfaces non-rugose, upper surface smooth, slightly glossy to very slightly glossy, lower surface smooth, dull, main vein sparsely covered with short hairs 1 mm in length, N155A in color.

*Leaf size*.—Up to 4.3 cm in length and 1.7 cm in width.

*Leaf color*.—Young upper surface NN137B, young lower surface 138A, mature upper surface NN137A, mature lower surface NN137D.

*Petioles*.—Average of 6 mm in length, 2 mm in width at widest point, 0.75 mm at narrowest point, strong, color; upper surface 145B to 146D, margins 137B, lower surface 146D, margins 137B, both surfaces slightly glossy, upper surface glabrous, lower surface glabrous with margins that are moderately to densely covered with short pubescent hairs 1.5 mm in length, N155A in color.

Inflorescence description:

*Inflorescence type*.—Terminal verticillaster.

*Lastingness of inflorescence*.—Individual flowers average of 10 days, very freely flowering, self-cleaning.

*Inflorescence size*.—An average of 12.6 cm in length and 2.1 cm in width.

*Flower type*.—Single, labiate.

*Flower number*.—An average of 70 flowers per inflorescence, 1,300 per plant.

*Flower aspect*.—Outward to slightly nodding, individual flowers twisted in an average angle of 45°.

*Flower fragrance*.—None.

*Flower buds*.—Obovate in shape, average of 4 mm in length and 2 mm in diameter, color; 143C, tinged 176B on the upper surface, immature sepals 63D, average of 1,700 per plant.

*Flower size*.—Average of 3.5 cm in length and about 8 mm in diameter, throat diameter 1 mm, tube length 3.5 mm, tube diameter 1.25 mm.

*Peduncle* (*rachis*).—Quadrangulate, an average of 15.2 cm in length and 1.8 mm in width, color 138A, strong, matte, surface is densely covered with very short hairs 0.3 mm in length, N155A in color, held at angles ranging between vertical and 30° to vertical.

*Pedicels*.—An average of 2 mm in length and 0.5 mm in width, color N77D, strong, matte, surface is densely covered with very short hairs 0.2 mm in length, N155A in color, angle ranging between 20° and 90°.

*Calyx*.—Campanulate, about 4.5 mm in length and 3 mm in width.

*Sepals*.—2, oblanceolate in shape, 55% fused, 4.5 mm in length, 2 mm in width, apex emarginate to praemorse, tip of sepal cleft, margins are moderately covered with very short glandular hairs average of 2 mm in length, too small to measure color, upper surface smooth and glabrous, matte, lower surface moderately pubescent with very short hairs; average of 0.5 mm in length, N155A, matte, color; upper surface when opening and fully open 145B, veined 144A, lower surface when opening and fully open 145B, veined 146B, upper sepal 143A, proximal end 145B, veined 176C.

*Petals*.—Labiate, 1 upper lip, 1 lower lip, average of 2 per flower, 1 whorl, lower 43.5% fused, upper lip; 4.5 mm in length, 1 mm in width, oblanceolate in shape and folded, emarginate tip, fused into tube, entire, non-undulate, glabrous, slightly velvety, lower lip densely pubescent with short hairs 0.5 mm in length, 75B in color, color; upper surface when opening and fully open 75D, lower surface when opening and fully open 75C to 75D, lower lip; 4.5 mm in length, 3.5 mm in width, spathulate in shape with two smaller lateral lobes, obtuse tip, fused into tube, entire, non- undulate, glabrous, slightly velvety, lower lip densely pubescent with short hairs 0.5 mm in length, 75B in color, color; upper and lower surface when opening and fully open between 75C and 76C, lower surface when opening and fully open 75C to 75D, upper and lower lip; throat and tube texture glabrous, slightly velvety, matte, flower throat color N75A, flower tube color N155A.

*Floral bracts*.—Below each whorl of flowers there are two bracts, oppositely placed, broad ovate to reniform in shape, 5 mm in length, 4 mm in width, broad cuneate base, top abruptly acute, both sides matte, smooth and glabrous, margins entire, moderately pubescent with very short hairs; average of 0.5 mm in length, N155A in color, both surfaces 143A in color, base 145D.

Reproductive organs:

*Gynoecium*.—Pistil; 1, average of 1.1 cm in length, 1.5 mm cleft, decurrent, style; 9 mm in length, 75B, base N155A, stigma; 1.5 mm in diameter, cleft, decurrent in shape, 70B in color, ovary; 169A to 169B, top 144A.

*Androecium*.—Stamens; 2, filaments; 76D in color, average of 1.5 mm in length, anthers; narrow oblong, 0.5 mm in length, 0.25 mm in width, 164B, pollen; none.

*Fruit and seed*.—Observed to be sterile with no viable seeds formed.

It is claimed:

1. A new and distinct cultivar of *Salvia* plant named 'Bocoffla' as herein illustrated and described.

* * * * *